US011246485B2

(12) United States Patent
Kall et al.

(10) Patent No.: US 11,246,485 B2
(45) Date of Patent: Feb. 15, 2022

(54) SYSTEM AND METHOD OF MONITORING ASSOCIATION BETWEEN WIRELESS SENSORS AND A MONITORED PATIENT

(71) Applicant: General Electric Company, Schenectady, NY (US)

(72) Inventors: Magnus Kall, Helsinki (FI); Tuomas Laine, Helsinki (FI); Mika Tapaninaho, Helsinki (FI); Oliver Mayer, Munich (DE); Sakari Lamminmaki, Helsinki (FI)

(73) Assignee: General Electric Company, Schenectady, NY (US)

( * ) Notice: Subject to any disclaimer, the term of this patent is extended or adjusted under 35 U.S.C. 154(b) by 539 days.

(21) Appl. No.: 15/387,829

(22) Filed: Dec. 22, 2016

(65) Prior Publication Data

US 2018/0177397 A1 Jun. 28, 2018

(51) Int. Cl.
*A61B 5/00* (2006.01)

(52) U.S. Cl.
CPC ............ *A61B 5/0024* (2013.01); *A61B 5/684* (2013.01); *A61B 5/6844* (2013.01); *A61B 5/743* (2013.01); *A61B 2560/0271* (2013.01)

(58) Field of Classification Search
CPC ... A61B 5/0015; A61B 5/6801; A61B 5/7221; A61B 5/742
See application file for complete search history.

(56) References Cited

U.S. PATENT DOCUMENTS

| 9,220,463 | B2 | 12/2015 | Grubis et al. | |
| 9,443,059 | B2 | 9/2016 | Grubis et al. | |
| 2012/0035427 | A1* | 2/2012 | Friedman | A61B 5/0002 600/300 |
| 2014/0081659 | A1* | 3/2014 | Nawana | G06F 19/00 705/3 |
| 2018/0116560 | A1* | 5/2018 | Quinn | A61B 5/1121 |

* cited by examiner

Primary Examiner — Lynsey C Eiseman
Assistant Examiner — Jessandra F Hough
(74) Attorney, Agent, or Firm — Andrus Intellectual Property Law, LLP

(57) ABSTRACT

Systems and methods of wireless sensing of physiological data includes obtaining physiological data from a patient with a wireless sensor. A patient location device determines a location of the patient. A location of the wireless sensor is obtained. The physiological data from the wireless sensor is associated to the patient based upon a determined proximity of the location of the wireless sensor to the location of the patient.

18 Claims, 5 Drawing Sheets

SYSTEM AND METHOD OF MONITORING ASSOCIATION BETWEEN WIRELESS SENSORS AND A MONITORED PATIENT

BACKGROUND

The present disclosure is related to the field of wireless sensing. More specifically, the present disclosure is related to evaluating an association between a wireless sensor and a monitored patient.

Monitoring vital signs is an important part of patient care as the general or particular health of the patient is determined, in part, through measurement and interpretation of key physiological indicators. Well-known parameters of patient health include blood pressure, oxygen saturation ($SpO_2$), and features of the electrocardiogram (ECG). However, the utilization of physiological instrumentation to obtain these measurements at the bed side of a patient also possesses well-known burdens to the clinical environment. The presence of cables, catheters, and tubing connecting the patient and sensors to the instrumentation configured to provide all monitoring or therapeutic care can diminish productivity and the quality of patient care. For example, rotating a patient to alleviate bed sores or ambulating about the room can be problematic if one is saddled with tethered devices. Procedural delays stemming from cable management also contribute to a great percentage of time dedicated to routine, mundane tasks not directly related to treatment of the patient's illness.

Wireless communication technology leveraged to patient monitoring may at least mitigate some of the problems associated with cable clutter and device management. With instrumentation becoming wireless, the management of such devices is eased. In addition, wireless instrumentation/devices greatly reduce the burden associated with cable management.

Wireless patient monitoring networks, however, bring new problems that need to be addressed for proper implementation of a wireless monitoring regime. In many instances, whether using a wireless monitoring system or a wired system, elements of the system communicate with at least one central management device. In the hospital environment, this management device is often used to relay monitored information to an infrastructure that allows health care professionals to analyze the monitored information from an outside location (e.g. a nurse station). In other wireless systems, the management device may be integrated with a central processing unit that analyzes the incoming device information. When cables are removed from these devices, a user of the system can no longer safe guard that the devices are properly connected to the patient to be monitored by the management device by simply ensuring that the cables extend from the management device to the correct patient. That is, without cables, a health care provider or other operator lacks the visual cues associated with cables to assure that the sensing devices are properly connected to the proper patient to be monitored by the management device. Alternatively, as wireless sensing systems proliferate in a care setting, wireless sensing devices may inadvertently become communicatively connected with a management device associated with another patient. Again, without the visual cues of the cable, a healthcare provider or other operator lacks a tool for fast and accurate confirmation that the management device is receiving physiological data from a specified patient and that patient only.

U.S. Pat. No. 9,220,463 discloses systems and methods of wireless monitoring. A plurality of peripheral electronic devices each having a wireless communication system. A processor is configured to establish an association confidence level indicative of a likelihood that a peripheral electronic device is associated to a monitored subject for each peripheral electronic device based on association criteria. Indicators are configured to communicate the association the association confidence level.

U.S. Pat. No. 9,443,059 discloses systems and methods of evaluating an association between a wireless sensor and a monitored patient. The systems and methods include a plurality of peripheral electronic devices each having a wireless communication system and a sensor. A processor receives measured physiological parameter data from the peripheral electronic devices and establishes an association status between each of the peripheral electronic devices and the monitored patient based upon identified characteristics in the physiological parameter data.

BRIEF DISCLOSURE

An exemplary embodiment of a system of wireless patient sensing includes a first wireless sensor comprising a physiological sensor configured to obtained first physiological data from a first patient. A patient location device is configured to determine a location of the first patient. A processor tracks a location of the first wireless sensor and receives the location of the first patient. The processor positions a model of the first patient at the received location of the first patient and compares the location of the first wireless sensor to the position model of the first patient. The processor associates the first physiological data to the first patient based upon the comparison. In an exemplary embodiment of a method of wireless sensing, physiological data wirelessly transmitted from a plurality of wireless sensors, is received. The location of each wireless sensor of the plurality of wireless sensors is obtained. A location of a first patient and a location of a second patient are obtained from at least one patient location device. A first model of the first patient is obtained and positioned at the location of the first patient. A second model of the second patient is obtained and positioned at the location of the second patient. The locations of each of the wireless sensors of the plurality of wireless sensors are compared to the positioned first model and the second model. The physiological data received from each wireless sensor of the plurality of wireless sensors is associated to the first patient or the second patient based upon a proximity of the location of each wireless sensor to the first patient model and the second patient model.

In an exemplary embodiment of a method of wireless sensing, a first plurality of wireless sensors are placed on a first patient. Each wireless sensor of the first plurality of wireless sensors obtains physiological data from the first patient. Each wireless sensor of the first plurality of wireless sensors transmits the obtained physiological data. The physiological data from the first plurality of wireless sensors is received at a processor. A location of each of the wireless sensors of the first plurality of wireless sensors is obtained. A model of the first patient is obtained and a location of the first patient is obtained. The obtained location of each of the wireless sensors of the first plurality of wireless sensors is compared to the model of the first patient positioned at the location of the first patient. The received physiological data is associated to the first patient based upon a proximity of each of the wireless sensors to the first patient represented by the model of the first patient positioned at the location of the first patient.

DETAILED DISCLOSURE

Figure 1:
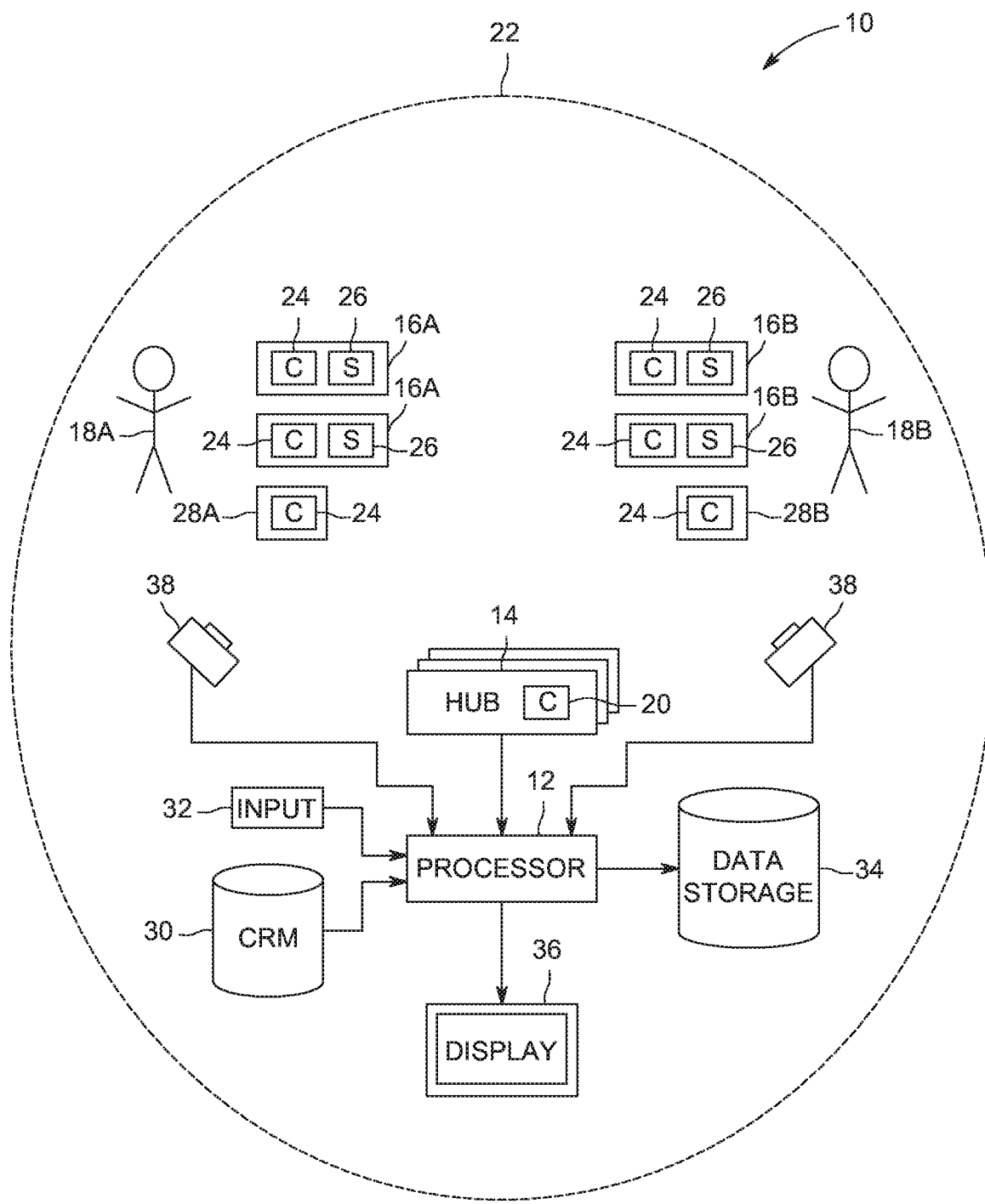
FIG. 1 is a schematic diagram of an exemplary embodiment of a wireless system.

FIG. 1 is a schematic diagram of a wireless system 10. The wireless system 10 includes a processor 12 that is configured in the manner as disclosed herein to receive a plurality of signals acquired by the wireless system 10 and evaluate the signals. The wireless system 10 further includes a hub 14 that is configured to communicate both with the processor 12 and with a plurality of wireless sensors 16 configured to be secured to a patient 18. It will be understood that in embodiments, the hub 14 may be an independent device that is communicatively connected to the processor 12, while in other embodiments the hub 14 may be integrated into a single device with the processor 12. In still further embodiments, the hub 14 may be a wearable device removably secured to a patient, while in other embodiments, the hub 14 may be one of many distributed throughout a care facility.

It will be recognized that in some embodiments, the processor 12 may be local to the hub 14 and/or the wireless system 10 generally. However, in other embodiments, the processor 12 may be remotely located across a communication network from the hub 14, for example in a cloud-based computing arrangement. In still further embodiments, the functionality as described herein attributable to the processor 12 may exemplarily be performed by multiple processors, for example in a distributed processing arrangement. The processor 12 may exemplarily operate in a similar manner as described herein under any of these arrangements and any such implementations are considered to be within the scope of the processor of the present disclosure.

The hub 14 includes a wireless communication system 20 that exemplarily creates a communication area or range 22 within which the hub 14 may be communicatively connected with one or more of the wireless sensors 16. The wireless sensors 16 further each include a wireless communication system 24. It will be understood that the wireless communication systems 20, 24 respectively of the hub 14 and the wireless sensors 16 will be communicatively compatible. In an exemplary embodiment, the wireless communication systems 20, 24 are radio frequency (RF) wireless communication devices. However, it will be understood that in alternative embodiments, the wireless communication systems 20, 24 may include optical, magnetic, ultrasound, visible light, infrared, or other forms of wireless communication systems.

While embodiments of the wireless sensors 16 may include other components as described in further detail herein, each of the wireless sensors 16 include at least one physiological sensor 26. The physiological sensor 26 is operable to acquire or measure at least one physiological parameter or signal. In the present disclosure, the exemplary embodiment and application of a health care setting is used for descriptive purposes, although, it will be recognized that alternative embodiments of the systems and methods as disclosed herein may be used in conjunction with other applications in which a plurality of personal wireless sensors must be managed. Thus, in the exemplary embodiment given herein, the physiological sensors 26 may be physiological sensors that are configured to acquire physiological data from a patient 18. In non-limiting embodiments, the physiological sensors 24 may include heart rate, pulse rate, temperature, electrocardiogram (ECG), blood pressure (e.g. NIBP), respiration, physical movement, electroencephalogram (EEG) and others as may be recognized by a person of ordinary skill in the art.

In embodiments, the sensors of the wireless sensors measure or otherwise acquire at least one physiological signal from the patient 18 and process the physiological signal as physiological data. The physiological data may be a digitized physiological signal or may be physiological data derived from a physiological signal obtained by the physiological sensor 26. For example, in the exemplary case of ECG, the physiological data may be a digitized ECG waveform or may be an instantaneous pulse rate derived from the ECG waveform. The wireless communication systems 24 of the wireless sensors 16 work with the wireless communication system 20 of the hub 14 to wirelessly transmit the acquired physiological data through the hub 14 to the processor 12.

The wireless system 10 further includes one or more patient location devices. Exemplary embodiments of patient location devices, as will be discussed in further detail herein, include patient location beacons 28 and cameras 38. The patient location devices exemplarily inform the wireless system 10 about the physical location of each of the patients 18A, 18B. As will be described in further detail herein, wireless sensors 16A, 16B are associated to a particular patient 18A, 18B based upon the physical location of the wireless sensor and proximity of that location to the detected location of a patient 18A, 18B.

Exemplary embodiments of patient location beacons 28 may be secured to a patient 18 and include a wireless communication system 24 which transmits a wireless signal or beacon, in any of a variety of communication modalities, including, but not limited to radiofrequency, ultrasound, or infrared which may be detected by a hub and/or hubs or another detection device (not depicted) configured to receive the signals from the patient location beacon 28. From the signals of the patient location beacons 28, a location of a particular patient can be identified. In exemplary embodiments, this may include triangulating the location of the patient based upon the detection of a signal from the patient location beacon 28 by two or more hubs 14 in order to locate the patient 28. In still further exemplary embodiments, multiple patient location beacons 28 may be secured to each patient 18. Exemplarily, patient location beacons secured to the patient 18 at multiple locations may provide a further refined indication of the location of the patient as described in further detail herein by identifying locations of multiple anatomical parts of the patient. For example, patient location beacons 28 located at two or more of the patient hip, shoulder, head, arm, hands, legs, or feet, may enable a more refined determination of the location of the patient and/or relative position of the patient's anatomy. This can result in a more refined model of the patient's body, as will be described herein with respect to some embodiments.

The patient location beacons 28 include communication systems 24 to transmit signals used to locate the beacons or to transmit another signal with location information to the system. A signal encoding location information may be received by one or more of the hubs 14. It will be recognized that in embodiments, the patient location beacons may communicate with the same hubs 14 with which the wireless sensors 16 communicate. Alternatively, the patient location beacons 28 may communicate with other hubs (not depicted) or other devices configured to send and/or receive communications from location beacons 28 in the event that a wireless communication platform is used by the patient location beacons 28 that is different from the one used by the wireless sensors 16 and the hubs 14.

Still further exemplary embodiments of patient location devices include cameras 38. In exemplary embodiments, one or more cameras 38 are distributed throughout an area wherein the wirelessly monitored patient or patients are expected to be. Object detection and tracking analysis in video and/or image data from the cameras 38 can be used to identify each of the patients 18A, 18B and to track the position and location of the patients 18A, 18B. Image data from two or more cameras can provide a stereo view from which depth and/or distance information for the location of the patient may be acquired. In other exemplary embodiments, a combination of infrared and regular cameras may be used while in still further embodiments digital cameras which incorporate time of flight distance measurements must be used to properly locate the patient in space. The patient may be detected in the image data from the cameras with image processing techniques. For example, this may be done using objects recognition software and other known techniques, including edge detection and pattern recognition. Once the patient is identified in the image data, the patient can be modeled in the manner as described in further detail herein. In embodiments, analysis of the image data from cameras 38 may be used to locate the patient as well as to provide or refine a patient model of the patient as described in further detail herein.

As depicted in FIG. 1, the wireless system 10 is particularly applicable for distinguishing the transmissions of wireless sensors 16 to associate the wireless sensors 16 with particular patients 18 when multiple patients 18A, 18B with wireless sensors 16A, 16B are monitored in a medical care facility. This is applicable with ambulatory patients who may move about a medical care facility and thus at any given time the wireless transmissions from the wireless sensors 16 associated with patients 18 may be received by one or more hubs 14 of a plurality of hubs 14 distributed throughout the medical care facility.

Currently available wireless monitoring solutions require a manual or partially automated registration process to associate each wireless sensor to a particular patient. This may exemplarily be currently performed using BLUETOOTH pairing with pin codes, near field communication (NFC) pairing, or WIFI direct printers, this registration processes is performed with manual interaction by a clinician with both the wireless sensors and the monitoring system to create an association between a signal of each wireless sensor and the patient to be monitored by that sensor. This manual registration processes offers opportunities for each wireless sensor to be incorrectly registered, and further uses a different association between each sensor and the patient to be monitored. Embodiments as disclosed herein provide an improved solution wherein by monitoring locations of the wireless sensors and the location of the patient, these locations may instead be used to associate the physiological data received from each of the wireless sensors to the particular patient from which the physiological data was obtained.

In exemplary embodiments, the wireless signals transmitted from each of the wireless sensors 16 are combined with location information for the wireless sensor making the transmission. As described in further detail herein, the wireless sensing system uses the location information of the wireless sensor in comparison to a determined location of the patient to sort the wireless signals from each of the wireless sensors between the various patients 18A, 18B being wirelessly monitored.

The processor 12 is connected to at least one computer readable medium 30. In embodiments, the processor 12 executes computer readable code stored on the computer readable medium 30 as software and firmware. The execution of the computer readable code causes the processor 12 to operate in a manner such as to carry out the operations and functions as described herein. In an exemplary embodiment, the computer readable medium 30 is an integral part of the processor 12.

An input device 32 is further connected to the processor 12 whereby a technician can enter information including information regarding patients to be monitored, the wireless sensors used, and/or the physiological conditions of the patients. In some embodiments as disclosed herein, the input device 32 may be used by the clinician or technician to enter or access information, for example stored in an electronic medical record (EMR) of a patient, regarding the patient to refine or improve a model of the patient as described in further detail herein.

The processor 12 is communicatively connected to the data storage 34, for example by a wired or wireless communication system. The data storage 34 may be located on a computer readable medium that is either local to or remote from the processor 12. In a non-limiting embodiment, the data storage 34 may be implemented in a cloud-based computing system that operates to manage the patient information, exemplarily in the EMR. Thus, the data storage 34 may be communicatively connected to the processor 12 through a local hospital intranet or a wide area network exemplarily over the Internet. In one embodiment, both the acquired physiological data received from the plurality of wireless sensors and the model of the patient used determine an association of the wireless sensors are stored in the data storage 34.

The processor 12 further operates a graphical display 36 that may be operated by the processor 12 to visually present the physiological data obtained by the system. In embodiments, the processor 12 may operate the graphical display 36 to additionally visually present indications of the wireless sensors from which the processor is receiving transmissions of physiological data and the patients to which each of the wireless sensors are associated. It will be recognized that the system as disclosed herein may be used in conjunction with other systems and methods for the association and identification of wireless sensors to patients. Thus, in such embodiments, the graphical display 36 may be further operated to present indications of lost wireless sensors, lost wireless sensor signals, or wireless sensor signals whose association with a patient has reduced confidence or is called into question. The graphical display 36 operates to present such information in a graphical user interface (GUI) which may be configured in a variety of manners to visually convey this information. In embodiments, the graphical display 36 may be a flat panel display or may be a display associated with a laptop or tablet computer, or a display of a mobile device. In still further embodiments, the display 36 may have touch sensitive capabilities and as such operate as both the display 36 as well as the input device 32. In still further embodiments, the display 36 may further be operated by the processor 12 to present some or all of the physiological data acquired from the monitored patient by the plurality of wireless sensors 16.

Figure 2:
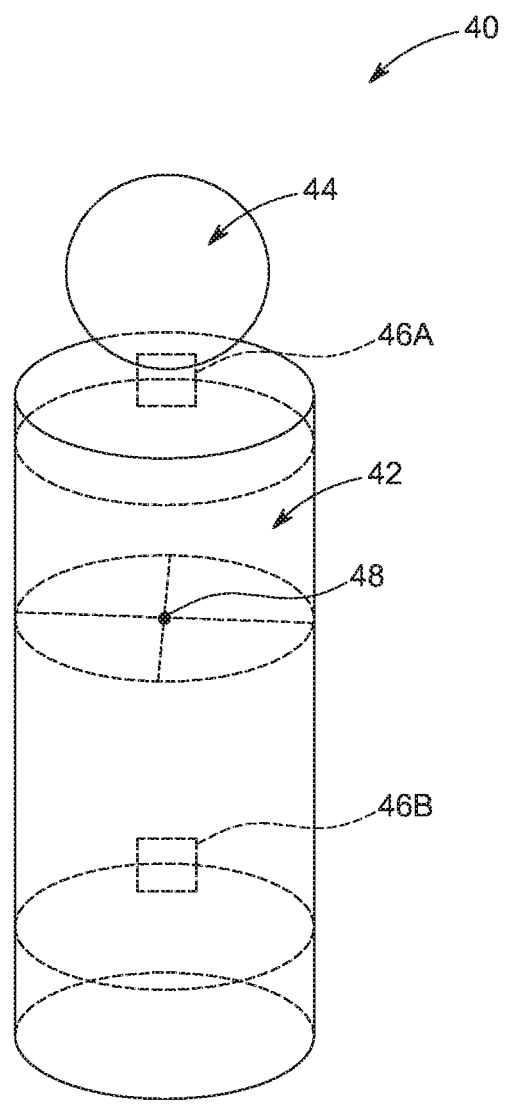
FIG. 2 depicts an exemplary embodiment of a patient model.

FIG. 2 depicts an exemplary embodiment of a patient model 40. It will be recognized that the patient model 40 exemplarily depicts a model with a base anthropomorphic shape including a body cylinder 42 and a spherical head 44. It will be further recognized that more complex or specifically tailored models may be produced with additional information regarding the patient, for example patient body type, height, head and torso dimensions, patient gender, and/or patient ethnicity. In exemplary embodiments wherein the location of the patient is determined using image data, the analysis of the image data may provide an outline or more specifically identified shape of the patient. While in embodiments, an identified shape extracted from the image data may be used as the patient model. In still further embodiments the identified shape of the patient from the image data is used to refine a patient model 40 in conjunction with other data as mentioned above. In an exemplary embodiment, patient anatomical data for example as identified above may be measure and/or extracted from the image data and incorporated into the patient model.

It will also be recognized that other exemplary embodiments of the patient model 40 may be more generalized than that specifically depicted in FIG. 2. More generalized patient models may exemplarily be used with those embodiments using one or more patient beacons. Patient beacons 46 are exemplarily represented in the model 40. The exemplary embodiment depicted in FIG. 2 visually represents two beacons 46, for example a beacon 46A positioned between the shoulder blade (not depicted) of the patient, and a beacon 46B located at the small of the patient's back (not depicted).

From these anatomical locations, a patient center of mass 48 may be determined. The center of mass determination may be a geometric determination between the anatomical reference points of the beacons 46A, 46b. This center of mass reference point may be further determined or the determination refined based upon patient anatomical or demographic information. In an exemplary embodiment, the patient center of mass for another single anatomical point of the patient may be used as a basic patient model 40. However, as described in further detail herein, a more refined patient model is exemplarily provided may provide more robust results. As mentioned above, a patient model 40 may be refined beyond a single point representing the location and/or position of the patient. The patient model may be refined to a center of mass estimation of the patient or a model based upon the connected locations of one or more beacons. In still further embodiments, the patient model may be a plurality of points. These points may exemplarily be the locations of the beacons on the patient. In another embodiment, these points may be geometrically connected. In still further embodiments, anatomical measurements for example a distance and direction of an anatomical feature such as the top of the patient's head, shoulder, hips, etc. from the locations of the beacons may be used to produce further points on the patient model.

As depicted in FIG. 2, the patient model 40 can be an anthropomorphic representation, exemplarily combining a cylinder or other geometric shape, including, but not limited to frustoconical representations. While such a shape may be used to represent an entirety of a patient, such a model may be further refined by providing a spherical or an ellipsoidal representation of a patient's head. Specific identification of the patient's head either in image data from cameras or from a patient location beacon placed on the patient's head can provide still further refinement as to the location and position of the patient's head relative to the torso.

In a still further exemplary embodiment, the patient model is refined beyond that which is depicted in FIG. 2 to define an outline of the patient as exemplarily provided by analysis of the image data from the cameras.

Figure 3:
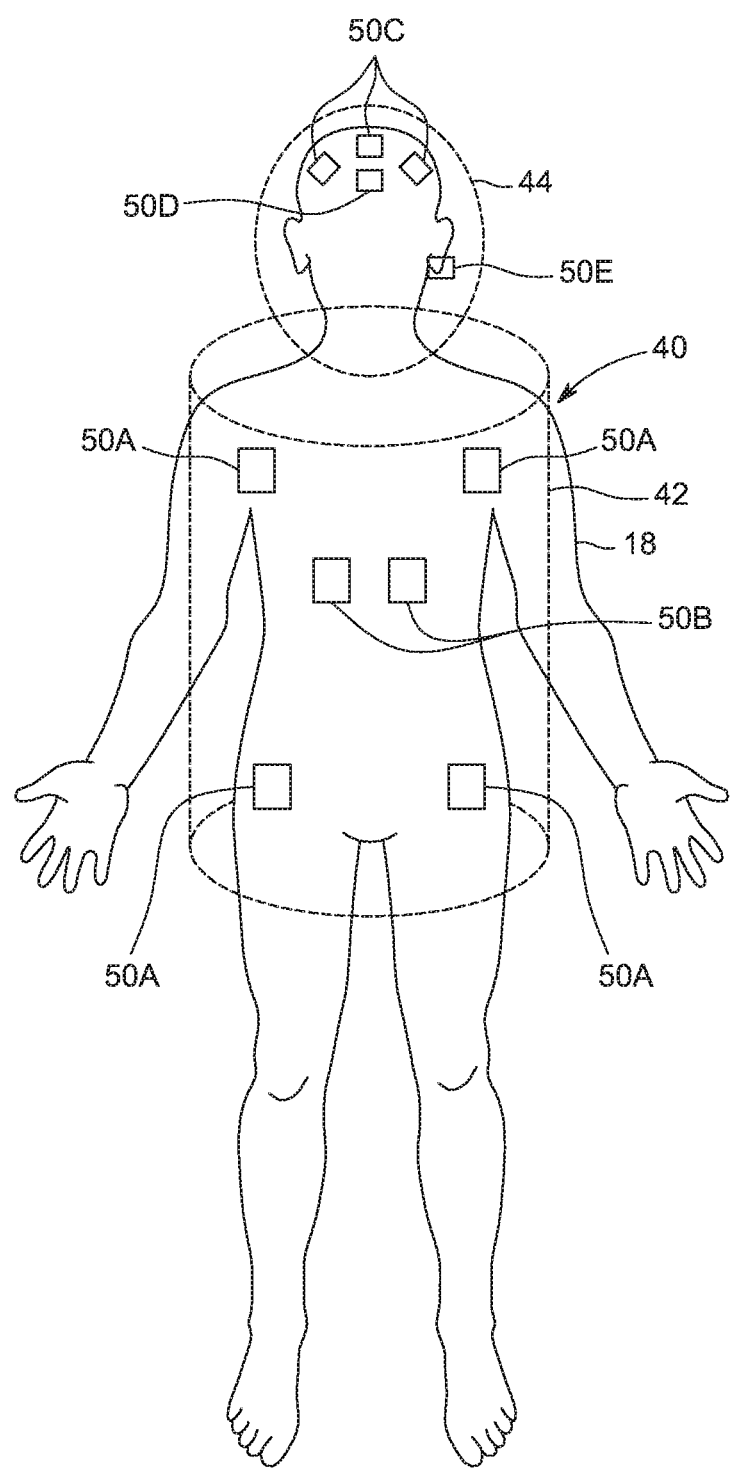
FIG. 3 depicts an exemplary embodiment of a patient model superimposed about a patient.

FIG. 3 exemplarily depicts a body of a patient 18 upon which a patient model 40 is superimposed. The patient model 40 exemplarily defines an envelope about the patient 18. In an exemplary embodiment, as described in further detail herein, physiological sensors 50 with locations determined to be within the envelope defined by the patient model 40 are associated to that patient. In other embodiments, the patient model 40 more closely defines the patient 18 and an envelope (not depicted) further defines a predetermined distance about the patient model 40 and physiological sensors 50 located within this envelope are associated to the patient 18 as described herein.

Exemplarily depicted in FIG. 3, the physiological sensors 50 exemplarily include electrocardiogram (ECG) sensors 50A, respiration sensors 50B, electroencephalogram (EEG) sensors 50C, a temperature sensor 50D, and an $SpO_2$ sensor 50E. These are exemplary and non-limiting embodiments of wireless physiological sensors 50 as may be positioned on the patient 18. The location of these physiological sensors, as determined by the system, if determined to be within the envelope about the patient are associated to the patient and the physiological data wirelessly received from these sensors is processed and stored in an electronic medical record of the associated patient.

Figure 4:
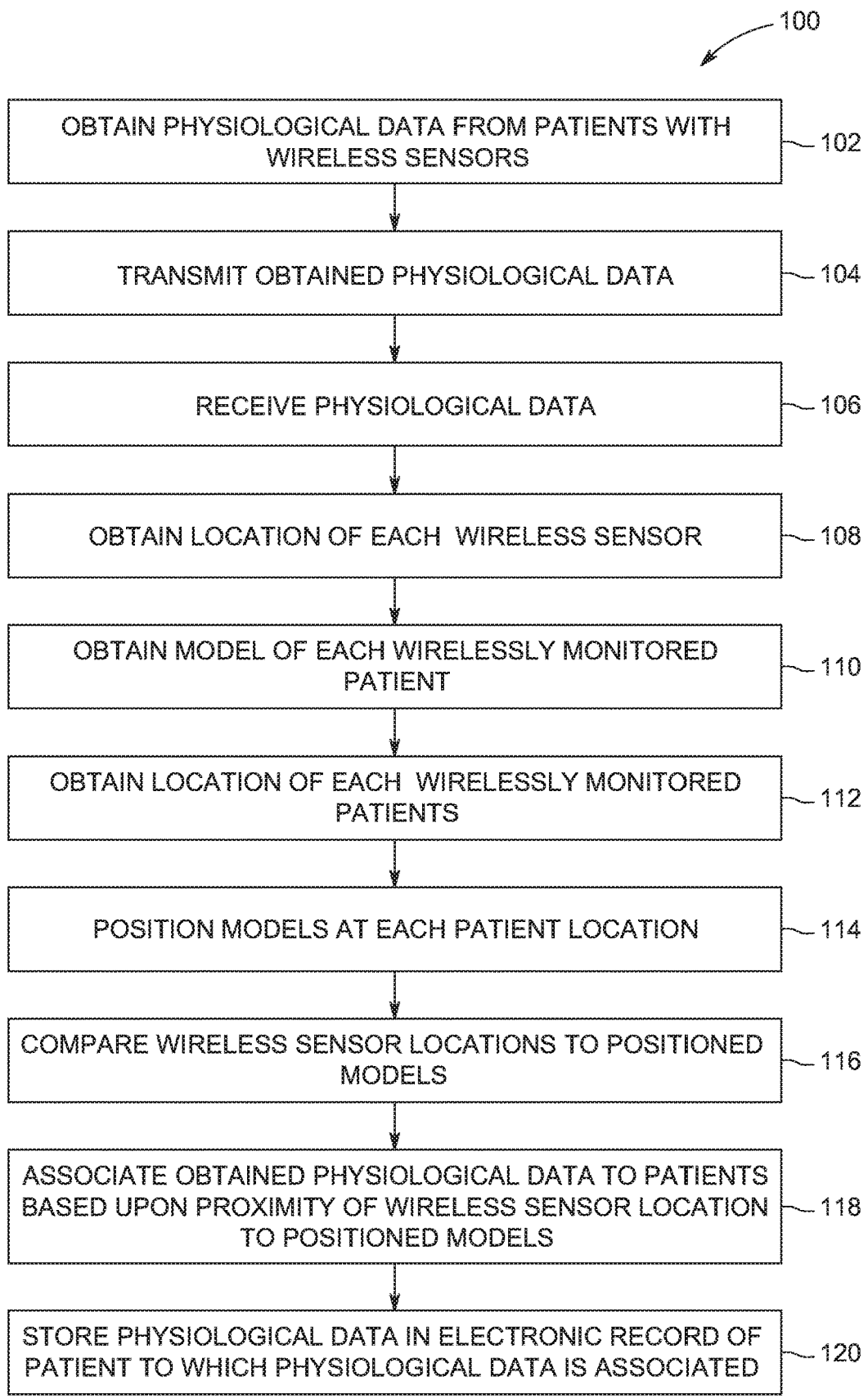
FIG. 4 is a flowchart that depicts an exemplary embodiment of a method of wireless sensing of physiological data.

FIG. 4 is a flow chart that depicts an exemplary embodiment of a method 100 of wireless sensing of physiological data. The method 100 may exemplarily be implemented through the use of the wireless system 10 depicted in FIG. 1 and described above.

An exemplary embodiment of the method of wireless sensing includes positioning wireless sensors on patients in a medical care facility, the physiological data of the patient intended to be wirelessly monitored. As described above, the medical care facility is exemplarily equipped with at least one communication system to receive transmissions of data from wireless sensors. The communication system may include at least one hub.

As noted above, embodiments of the method 100 as described herein can be used to accurately sort the physiological data of multiple patients wirelessly received by the communication system into the electronic records of the appropriate patient without the need to specifically register each wireless sensor in the system to a specific patient through a manual or a semi-manual registration process.

At 102 physiological data is obtained from the patients with wireless sensors on those patients. Sensors integrated into the wireless sensors transduce physiological signals from the patient to obtain physiological data. The wireless sensors at 104 wirelessly transmit the obtained physiological data. At 106 a processor receives the physiological data transmitted by the wireless sensors. In exemplary embodiments, a communication network, may include a plurality of hubs distributed through the medical are facility elects the transmission of physiological data from each of the wireless sensors and provides physiological data to the processor. In other exemplary embodiments as noted above, the processor may be remotely located from the wireless sensors, for example in a cloud-based implementation with communication exemplarily provided through the Internet.

Next, a location of each of the wireless sensors of the plurality of wireless sensor is obtained at 108. As noted above, in embodiments, the communication system may be capable of detecting the transmissions of the physiological data from the wireless sensors from two or more locations, enabling the triangulation of the location of each of the wireless sensors for example based upon time of flight differences between the received transmissions. It will be recognized that in embodiments another way for determination of location may include the incorporation of a location identification system into a patient beacon or a wireless sensor, for example global position system (GPS). The beacon or wireless sensor may operate to transmit a location signal for example as provided by the GPS. In another embodiment, location signals may be broadcast about the medical care facility, which are received and returned by each of the patient location beacons and/or wireless sensors to provide information regarding the location of each of these devices.

Next, at 110, the model of each wirelessly monitored patient is obtained. In exemplary embodiments, a predefined model may exemplarily be used for each of the wirelessly monitored patients. The model may exemplarily be anthropomorphic in shape, including, but not limited to a model with roughly anthropomorphic geometric features. In further embodiments, a generalized model may be modified or a more personalized model created by the incorporation of anatomic data of each specific patient into the model. Specific dimensions of the patient including, but not limited to, head circumference, shoulder width, or patient height may be used to refine a model to tailor the model to the patient. Still further anatomic and/or demographic information including selection between generalized body types, patient weight or body mass index (BMI), patient gender, age, or ethnicity, may help to further tailor the model to the specific patient.

In other exemplary embodiments, the model of each wirelessly monitored patient may be a point or a series of points which generally represent the patient, for example, including but not limited to a patient center of mass. In still further exemplary embodiments, particularly embodiments wherein image detection analysis is used to track the patient, a 3D model or partial model of the patient may be constructed. This patient model may be obtained based upon image data of the patient which may include, but is not limited to visual image data, infrared image data, for example from the cameras as used to track the location of the patient. In still further embodiments, image data obtained from other medical imaging operations, including, but not limited to CT, MRI images of the patient may be used to construct the patient model. The models of the patient may exemplarily be previously created and stored, for example, in an electronic medical record of the patient, or may be created at 110 for use in implementation of the method as described herein.

At 112, a location of each of the wirelessly monitored patients is obtained. As described above, the location of each of the wirelessly monitored patients may be obtained using at least one patient location device. In exemplary embodiments, the at least one patient location device may exemplarily be a camera or a plurality of cameras distributed through the medical care facility and configured to capture images of the patient which can be processed using image processing techniques to detect the patients and identify a location of the patient within the medical care facility based upon the image analysis. In other exemplary embodiments, at least one patient location device may be one or more patient location beacons secured to the patient, the location of which may be tracked to provide an indication of the location of the patient and/or anatomical reference points of the patient. In non-limiting and exemplary embodiments, patient location beacons may be secured to anatomical reference locations, for example the small of the back, between the shoulder blades, and on the patient's head to provide separate determinations of the location of these anatomical reference points of the patients.

In still further exemplary embodiments, the at least one patient location device may include two or more modalities, for example visual image cameras and infrared image cameras and/or ultrasound to further provide additional information which can be used to identify the location of the patient. Such embodiments may include the ability to obtain distance information, for example using time of flight measurements. In additional embodiments, both patient location beacons and cameras may be used to track patient location. In an exemplary embodiment, one or more patient location beacon may be used to determine a position of the patient, while image data from one or more cameras may be used to determine the orientation of the patient, for example, sitting, standing, laying down, which direction f the patient is facing, etc. these additional determinations of patient orientation may further help or be used in properly locating the patient model.

Next, at 114 the models of each of the wirelessly monitored patients are positioned at the locations of each of the wirelessly monitored patients. Positioning of the model at each of the locations of the patients may include determining an orientation of the patient at the patient's location and accurately positioning the model thereon. In such embodiments, when two or more reference points of the location of the patient, for example the locations of particular anatomical features of the patient can help in accurately positioning the patient model at the location of the wirelessly monitored patient. For example, by determining the position of both shoulder of the patient the direction the patient is facing can be narrowed to two directions. By determining at least one more anatomical point on the patient offset from the frontal plane can refine this determination to identify the direction the patient is facing. In an embodiment using cameras, as discussed above, image processing of the image data may be used to identify anatomical features to determine the orientation of the patient.

At 116, the obtained locations of each of the wireless sensors can be compared to the patient models positioned at each of the patient locations. In exemplary embodiments, the patient models may define an envelope within which if a wireless sensor is located, that wireless sensor is determined to be associated to a particular patient. In another embodiment, the patient models represent the patient and a patient envelope is further defined at a predetermined distance outwards from the patient model and wireless sensors located within that patient envelope are determined to be associated with the patient. In non-limiting examples, the patient envelope may be five centimeter exterior of the patient model, while in other embodiments, this distance may be greater or smaller.

Based upon the comparison of the wireless sensor locations to the position of the patient models, the obtained physiological data is associated at 118 to a particular patient of the plurality of wirelessly monitored patients. In an embodiment, this means that if a wireless sensor is determined to be located within a properly positioned patient model or within a patient envelope about a patient model the physiological data from that wireless sensor is associated to that patient. In a still further exemplary embodiment, the proximity of the wireless sensor locations to the positioned models are further tracked over time and a predetermined time threshold of the wireless sensor location being within a predetermined proximity of the patient model must be met and maintained prior to associating the physiological data from that wireless sensor to the patient of the model. In an exemplary embodiment, this may help to protect against two patients being temporarily located in close proximity to one another from interfering with the proper association of the wireless sensors to the patient from which the physiological data was obtained.

At 120, the physiological data obtained from the wireless sensor is stored in an electronic medical record of the patient to which the wireless sensor which obtained the physiological data is associated. Exemplary embodiments of the method as disclosed herein provide for the collection and sorting of received transmissions of physiological data from wireless physiological sensors without the need to specifically pre-register any of the wireless sensors with a specific patient, but rather by tracking the location of the wireless sensors and of the wirelessly monitored patients can sort the physiological data after it has been received.

Figure 5:
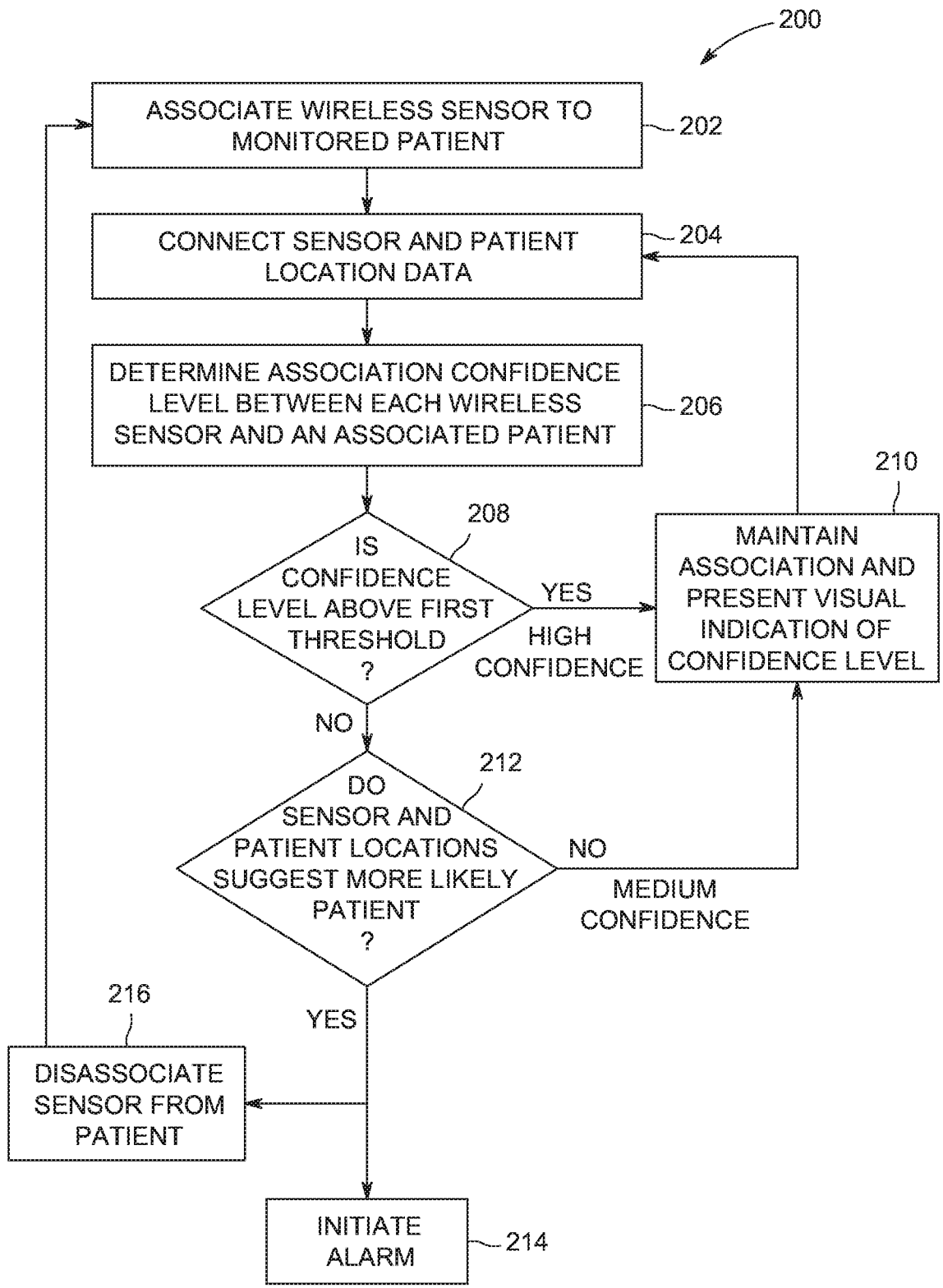
FIG. 5 is a flowchart that depicts an exemplary embodiment of a method of evaluating an association between a wireless sensor and a monitored system.

FIG. 5 is a flowchart that depicts an exemplary embodiment of method 200 of a evaluating an association between a wireless sensor and a monitored patient. The method 200 may be carried out by a wireless system, such as wireless system 10 described above. It will be understood that in alternative embodiments and in association comments level can be determined according to the method 200 or within other exemplary systems. While embodiments as described above have focused on associating transmission from particular wireless sensors to a particular patient being monitored by each wireless sensor, in other embodiments the systems and methods as described herein may be used to evaluate an association between a wireless sensor and a patient on an ongoing basis, after initial registration or association has been made. In embodiments, as described herein, such determination of association confidence may be made independently from or in conjunction with other measures of association confidence.

In an embodiment, location data regarding each patient and each sensor of a plurality of sensors is used to associate physiological data from each wireless sensor to a patient. During use, association criteria which include at least the location of the wireless sensor and the location of the patient and patient model is evaluated to determine an association confidence level between the wireless sensor and the monitored patient. Depending upon the sensor itself, the type of wireless communication system used by the sensor, and the components available in the wireless sensor, which may include, but are not limited to a clock or a battery, certain system and sensor attributes as described in further detail here may also be used as association criteria in calculating the association confidence level.

At 202, each wireless sensor of the plurality of wireless sensors is associated to a monitored patient. The wireless sensors may be associated to a patient by the manners as described above or may be associated and/or registered to a patient by one or more clinician or technician inputs into the wireless system in order to provide an initial association between each of the plurality of wireless sensors and the patient to be monitored. After the wireless sensors are associated and/or registered to the monitored patient, the processor may begin to receive physiological data acquired by the sensors through the wireless system.

The physiological data acquired by the sensors may be received throughout the wireless system wherein the wireless sensors transmit the physiological data to a processor as described above. As further described above, a variety of physiological data may be acquired by sensors in the wireless system. The received physiological data may include, but is not limited to ECG, EMG, EEG, temperature, respiration, $SpO_2$, blood pressure, movement, heart rate, pulse rate, or other forms of physiological data as will be recognized by a person of ordinary skill in the art. Depending upon the diagnosis and treatment being received by the patient, the patient may be monitored to acquire various physiological data. In embodiments, the acquired physiological data may be in the exemplary forms of wave forms, traces, or other signals that may be processed to obtain values meaningful to determining an association confidence level.

At 204 sensor and patient location data is collected from the wireless system in the manners as described above. As noted above, the sensor and patient location data can be obtained in a variety of manners, including, but not limited to position detection, for example by a real-time location system (RTLS), and analysis of image data. This is used at 206 to determine an association confidence level for each wireless sensor to the associated patient. The association confidence level can be determined for each wireless sensor based at least in part upon the monitored location of the wireless sensor relative to the monitored location of the associated patient and the patient model of the associated patient. Additionally, it will be recognized that in embodiments, the association confidence level may be further determined based upon additional information. This additional information may include other information acquired from the wireless sensors, including system data which may include values and/or conditions that are related to the association of the wireless sensor to the monitored patient, but are a part of the wireless system rather than physiological data acquired from the patient. Examples of association criteria that may be used to determine the association confidence level may be dependent upon system data and can include, but are not limited to: a length of time since registration or association of the wireless sensor to a patient, an RF signal strength of the wireless sensor, and elapsed time that peripheral electronic device is confirmed off of a patient, activity types, a number of communication errors, a battery state or condition, a known operational life time of the wireless sensor, an elapsed time on a patient, identified instances of sensor disconnection from the patient; however, these are merely exemplary of the types of associated criteria that may be collected from the system.

Additionally, in still further embodiments, physiological data collected by the wireless sensor may be used in part to determine an association confidence level for example by correlating the signals obtained by multiple sensors for example to monitor similarities in physiological data acquired from the same patient. For example, wireless sensors monitoring ECG, heart rate, pulse, SpO2, etc., should all produce correlated measurements to one another as each of the sensors as presumably measuring the physiological activity of the same patient. Association criteria values used in determining an association confidence level may be derived from the physiological data and the system data.

In exemplary embodiments, the association criteria referenced above, including, but not limited to the position of the wireless sensors relative to the position of the patient may be weighted. Weighting criteria may be determined based upon an overall strength of each of the association criteria as well as a total number of the association criteria available in the set of available association criteria used in making the determination. Weighing criteria may also be further determined based upon the drive valves of the association criteria. The relative strength of the association criteria and determining an association confidence level between a wireless sensor and a monitored patient may be considered in weighting the association criteria. For example, an association criteria such as elapsed time since initial registration may be heavily weighted if the elapsed time is short, but may receive a lesser weighting as the elapsed time lengthens. In an embodiment, the weighting may again increase, as an indicator of decreased confidence, if the elapsed time exceeds an expected procedure duration or wireless sensor expected usage. It is to be noted that in some embodiments, only the determined locations of the wireless sensors and the associated patients may be used to determine the association confidence level while in other embodiments, a combination of the determined locations used in addition to association criteria based upon system data and/or physiological data may be used as well.

During monitoring of the physiological data using the wireless sensors, the determined association confidence level may be used to continuously and/or periodically monitor and evaluate the confidence that each of the wireless sensors, and the physiological data measured by those wireless sensors, are properly associated to the correct patient. At 208, the confidence level determined at 206 is exemplarily compared to a first threshold. As noted above, the association confidence level, produced at 206, may be a numerical value that is capable of being compared to a threshold value. The first threshold value may exemplarily be representative of a high confidence in the association between that wireless sensor and the monitored patient. In a merely exemplary embodiment, the association confidence level from 206 may be on a scale of 0-100 and the first threshold may exemplarily be a normalized score of 90 although the first threshold may be any value and deemed medically or institutionally relevant.

In an exemplary embodiment, if there are no other patients in the vicinity of the monitored patient, or the wireless sensors, that may exemplarily result in an association confidence level that is meeting the criteria of the first threshold.

At 210, the association between the wireless sensor and the monitored patient is maintained, and in a further exemplary embodiment, a visual indication of the determined association confidence level may be presented. In non-limiting examples the confidence level may be presented in a graphical user interface presented on a display and such presentation may include a presentation of a numerical association confidence level, a value and/or a categorization of such association confidence level. In a non-limiting embodiment, such categorization may be an indication of a high confidence, medium confidence, or low confidence as described in further detail herein. In still further exemplary embodiments, the association confidence level may be transmitted back to the wireless sensors and a visual indicator on the wireless sensor, exemplarily one or more light emitted diodes (LEDs), may be illuminated at a color or intensity representative of the association confidence level.

At 212, if the association confidence level determined at 206 is determined to be below the first confidence level, and therefore the first analysis did not result in a high or first level of confidence in the association, then at 212 an analysis is made to determine if the sensor and patient location data suggests a more likely patient to which the sensor may be associated. In an exemplary embodiment, a determined location of a wireless sensor may produce an ambiguous relation to the associated patient, for example due to limits in resolution of the monitoring system or temporary obstruction of a wireless sensor or other potential sources of error in sensor or patient location determination. If there are no other more likely wirelessly monitored patients in the vicinity of the wireless sensor, then the existing association between the wireless sensor and a monitored patient is maintained at 210 yet the visual indication of the confidence level that is presented may be modified to reflect a medium or otherwise reduced level of confidence in the association. Such an embodiment may also be useful in an exemplary case wherein two wirelessly monitored patients are in close proximity to one another and therefore, the wireless sensors associated with each of those wirelessly monitored patients may produce ambiguous association confidence levels based upon the intermingling locations of the wireless sensors relative to the determined locations of the two or more patients. In a still further exemplary embodiment, as described above when the wirelessly monitored patients are represented by patient models positioned at the determined patient locations, it is possible that when two patients are located in close proximity, one or more wireless sensors may be determined to be located at or within patient models simultaneously. In an exemplary embodiment, by maintaining an existing association in the event of ambiguous association confidence determination, the system may be able to handle such conditions, particularly when such conditions may be temporary or short in time duration without raising further alarm or taking further action as described herein, resulting in a potentially more robust monitoring system.

However, in the event that at 212 the sensor and patient locations suggest a more likely patient association than the current monitored patient to which the wireless sensor is associated, then at 214 an alarm may be initiated to alert the clinician or technician to the determination. This may exemplarily presented on aforementioned graphical display or may be transmitted to the wireless sensor itself for an initiation of an alarm, e.g. visual, audio, or tactile (e.g. vibratory) indications.

At 216, the wireless sensor may also be disassociated from the monitored patient. In such an embodiment, the physiological data obtained by the wireless sensor may still be temporarily stored, but may not be immediately entered into an electronic medical record of the previously associated monitored patient, or any other wirelessly monitored patient until the association can be resolved. In still other exemplary embodiments, the physiological data from the affected sensor may continue to be presented on a graphical display along with the other physiological data obtained from a monitored patient, but with a further indication that the association between this data and the monitored patient is low or questioned. These actions may exemplarily be done as a precaution such that physiological data in which there is a low confidence to have emanated from the associated monitored patient, and more specifically physiological data which is suggested to rather be associated to a different patient, is not immediately stored or presented in conjunction with the physiological data of the previously associated monitored patient. Since the confidence is low that this physiological data is properly attributed to the previously associated monitored patient, it may be preferable to take the precaution such that medical decisions, diagnosis, and other such determinations are not made based upon this physiological data. If, at a later time, the wireless sensor is verified to have been associated with the monitored patient or another monitored patient at the time that the data was acquired, the physiological data that was temporarily stored may be transferred to the properly associated patient's electronic medical record. The physiological data may also be stored at one patient's medical record with an indication, flag, or other notation that the physiological data has a low or reduced association confidence level, for example until a revised or improved association to another patient is made at which time the physiological data could be transferred to the other patient's medical record. In an alternative embodiment, once a wireless sensor is disassociated from a monitored patient, the wireless system may no longer process or store any physiological data acquired by that wireless sensors until the wireless sensor is re-registered or re-associated to a monitored patient.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system of wireless patient sensing, the system comprising:
   a first wireless sensor comprising a physiological sensor configured to obtain first physiological data;
   a patient location device configured to determine a location of a first patient;
   a processor configured to determine a location of the first wireless sensor and to receive the location of the first patient from the patient location device, the processor configured to digitally position a digital model of the first patient at the location of the first patient and compare the location of the first wireless sensor to the positioned digital model of the first patient and assign the first physiological data to the first patient based upon the comparison;
   wherein the model of the first patient is an anthropomorphic model; and
   wherein the first physiological data is assigned to the first patient if the location of the first wireless sensor is within a predetermined distance of an envelope of the model of the first patient.

2. The system of claim 1, further comprising a plurality of hubs, wherein the processor triangulates the location of the first wireless sensor based upon signals from the first wireless sensor received by at least two of the plurality of hubs.

3. The system of claim 1, where the patient location device comprises a plurality of cameras and the processor processes image data from the plurality of cameras to determine the location of the first patient.

4. The system of claim 1, wherein the patient location device comprises at least one patient location beacon secured to the first patient, the patient location beacon broadcasts a signal tracked by the processor to receive the location of the first patient.

5. The system of claim 1, wherein the model of the first patient incorporates anatomical data of the first patient to personalize the model to the first patient.

6. The system of claim 5, wherein the patient location device comprises a plurality of patient location beacons secured to the first patient, each of the patient location beacons broadcasts signals tracked by the processor to receive the location of the first patient.

7. The system of claim 6, wherein the patient location beacons are placed at specific anatomical locations on the first patient and the model of the first patient comprises measurements between the locations of the patient location beacons.

8. The system of claim 1, wherein the patient location device is a first patient location device and further comprising:
   a second patient location device configured to determine a location of a second patient; and
   a second wireless sensor comprising a physiological sensor configured to obtain second physiological data;
   wherein the processor determines a location of the second wireless sensor and receives the location of the second patient from the second patient location device, the processor positions a model of the second patient at the location of the second patient and compares the location of the second wireless sensor to the positioned models of the first patient and the second patient and assigns the second physiological data to the first patient or the second patient based upon the comparison.

9. A method of wireless sensing of physiological data, the method comprising:
   receiving physiological data wirelessly transmitted from a plurality of wireless sensors;
   obtaining a location of each wireless sensor of the plurality of wireless sensors;
   obtaining from at least one patient location device, a location of a first patient and a location of a second patient;
   obtaining a first model of the first patient and positioning the first model at the obtained location of the first patient, wherein the first model of the first patient is an anthropomorphic model;
   obtaining a second model of the second patient and positioning the second model at the obtained location of the second patient, wherein the second model of the second patient is an anthropomorphic model;
   comparing the locations of each of the wireless sensors of the plurality of wireless sensors to the first model positioned at the obtained location of the first patient and the second model positioned at the obtained location of the second patient; and
   assigning the physiological data received from each wireless sensor of the plurality of wireless sensors to the first patient or the second patient based upon a proximity of the location of each wireless sensor to the first model and the second model, wherein the physiological data is assigned to the first patient if the location of the wireless sensor is within a predetermined distance of an envelope of the first model of the first patient and is assigned to the second patient if the location of the wireless sensor is within the predetermined distance of an envelope of the second model of the second patient.

10. The method of claim 9, further comprising sorting the received physiological data from the plurality of wireless sensors between electronic records of the first patient and the second patient based upon the association of the physiological data to the first patient or the second patient.

11. The method of claim 9, further comprising:
calculating an association confidence level between each of the wireless sensors and the first patient; and
evaluating the association between the first patient and each of the wireless sensors based upon the calculated association confidence levels.

12. A method of wireless sensing of physiological data, the method comprising:
placing a first plurality of wireless sensors on a first patient;
each wireless sensor of the first plurality of wireless sensors obtaining physiological data from the first patient;
each wireless sensor of the first plurality of wireless sensors transmitting the obtained physiological data;
receiving the physiological data from the first plurality of wireless sensors at a processor;
determining a location of each of the wireless sensors of the first plurality of wireless sensors;
obtaining a model of the first patient, wherein the model of the first patient is an anthropomorphic model;
determining a location of the first patient with a patient location device;
comparing the determined location of each of the wireless sensors of the first plurality of wireless sensors to the model of the first patient positioned at the determined location of the first patient;
assigning the received physiological data to the first patient based upon a proximity of each of the wireless sensors to the first patient represented by the model of the first patient positioned at the location of the first patient, wherein the physiological data from each of the wireless sensors is assigned to the first patient if the location of the first wireless sensor is within a predetermined distance of an envelope of the model of the first patient; and
calculating an association confidence level between each wireless sensor of the first plurality of wireless sensors and the first patient from the location of each of the wireless sensors and the model of the first patient positioned at the location of the first patient.

13. The method of claim 12, further comprising evaluating the association confidence level between each wireless sensor of the first plurality of wireless sensors and the first patient to determine if the association between each wireless sensor of the first plurality of wireless sensors with the first patient should be maintained.

14. The method of claim 13, further comprising comparing obtained locations of each of the wireless sensors of the first plurality of wireless sensors to a model of a second patient positioned at a location of a second patient to calculate an association confidence level between each of the wireless sensors and the second patient.

15. The method of claim 14, further comprising:
evaluating, for each wireless sensor, if the association confidence level is greater between the wireless sensor and first patient or the second patient; and
associating the wireless sensor to the first patient or the second patient based upon the evaluation.

16. The system of claim 1, wherein the processor is configured to calculate a first assignment confidence level between the first physiological data and the first patient and evaluate the assignment of the first physiological data to the first patient based on the first assignment confidence level.

17. The system of claim 16, wherein the processor is configured to calculate the first assignment confidence level by recomparing the location of the first wireless sensor to the positioned model of the first patient.

18. The system of claim 8, wherein the processor is configured to calculate an assignment confidence level between at least one of the first physiological data and the second physiological data and at least one of the first patient and the second patient; and
the processor is configured to evaluate at least one of the assignment of the first physiological data and the assignment of the second physiological based on the assignment confidence levels.

* * * * *